United States Patent
Silverman

(10) Patent No.: US 9,877,800 B1
(45) Date of Patent: Jan. 30, 2018

(54) NON-INVASIVE METHOD OF MAKING A TOOTH VENEER

(71) Applicant: Harvey Silverman, Pepper Pike, OH (US)

(72) Inventor: Harvey Silverman, Pepper Pike, OH (US)

( * ) Notice: Subject to any disclaimer, the term of this patent is extended or adjusted under 35 U.S.C. 154(b) by 595 days.

(21) Appl. No.: 14/249,507

(22) Filed: Apr. 10, 2014

Related U.S. Application Data

(60) Provisional application No. 61/810,989, filed on Apr. 11, 2013, provisional application No. 61/863,250, filed on Aug. 7, 2013.

(51) Int. Cl.
*A61C 5/00* (2017.01)
*A61C 19/06* (2006.01)

(52) U.S. Cl.
CPC ............ *A61C 5/002* (2013.01); *A61C 19/066* (2013.01)

(58) Field of Classification Search
CPC .. A61C 5/00; A61C 5/002; A61C 5/08; A61C 5/10; A61C 13/00; A61C 13/0001; A61C 13/001–13/0019; A61C 13/34; A61C 13/08–13/097; A61C 19/066
USPC ..... 433/167, 180–183, 191–195, 213, 217.1, 433/226
See application file for complete search history.

(56) References Cited

U.S. PATENT DOCUMENTS

| | | | | | |
|---|---|---|---|---|---|
| 3,986,261 | A | * | 10/1976 | Faunce | A61C 5/00 433/217.1 |
| 4,115,487 | A | * | 9/1978 | Rockett | A61C 13/09 264/16 |
| 4,226,593 | A | * | 10/1980 | Cohen | A61C 5/002 433/213 |
| 4,380,435 | A | * | 4/1983 | Raeder | A61C 13/26 433/180 |
| 4,433,959 | A | * | 2/1984 | Faunce | A61C 5/00 106/35 |
| 4,604,059 | A | * | 8/1986 | Klaus | C04B 33/24 106/35 |
| 4,822,278 | A | * | 4/1989 | Oliva | A61C 3/00 294/189 |

(Continued)

OTHER PUBLICATIONS

Dental Products Report; How to Place Monomer Technology Composite; Feb. 17, 2010; Frank J. Milnar, DDS.

(Continued)

*Primary Examiner* — Stephen R Crow
*Assistant Examiner* — Garrett Atkinson
(74) *Attorney, Agent, or Firm* — Shlesinger, Arkwright & Garvey LLP

(57) ABSTRACT

A non-invasive method for making a tooth veneer from composite resin material for a patient's tooth without tooth reduction, enamel removal or any invasive tooth preparation, comprising the steps of transferring an amount composite resin material on the patient's tooth without prior invasive tooth preparation; forming a preview veneer from the composite resin material directly on the tooth; requesting the patient to approve or disapprove the preview veneer; if approved, requesting the patient whether to have a first method veneer or a second method veneer. A kit for a non-invasive method of making a tooth veneer for a patient's tooth without tooth reduction, enamel removal or any invasive tooth preparation.

25 Claims, 9 Drawing Sheets

(56) References Cited

U.S. PATENT DOCUMENTS

| | | | |
|---|---|---|---|
| 4,850,875 A * | 7/1989 | Takatsu | A61C 5/00 433/119 |
| 4,895,516 A * | 1/1990 | Hulten | A61C 13/0003 264/16 |
| 4,992,049 A | 2/1991 | Weissman | |
| 5,000,687 A | 3/1991 | Yarovesky et al. | |
| 5,183,397 A | 2/1993 | Weissman | |
| 5,183,834 A | 2/1993 | Gorlich et al. | |
| 5,624,261 A | 4/1997 | Wiedenfeld | |
| 5,624,262 A | 4/1997 | Yarovesky et al. | |
| 5,975,906 A | 11/1999 | Knutson | |
| 5,984,682 A | 11/1999 | Carlson | |
| 5,997,302 A | 12/1999 | Alpert | |
| 6,102,705 A * | 8/2000 | Darnell | A61C 5/00 433/216 |
| 6,579,919 B2 | 6/2003 | Konings et al. | |
| 7,214,262 B2 * | 5/2007 | Hurwitz | A61K 6/0017 106/35 |
| 7,229,286 B2 | 6/2007 | Jones et al. | |
| D567,380 S | 4/2008 | Huffman | |
| 7,442,040 B2 | 10/2008 | Kuo | |
| 8,043,092 B2 | 10/2011 | Stonisch | |
| 8,057,231 B2 | 11/2011 | Viscomi | |
| 8,197,252 B1 | 6/2012 | Harrison, III | |
| 8,376,745 B2 | 2/2013 | Stonisch | |
| 8,377,500 B2 | 2/2013 | Yarovesky | |
| 8,834,161 B2 * | 9/2014 | Vult Von Steyern | A61C 13/081 264/681 |
| 2001/0012608 A1 * | 8/2001 | Darnell | A61C 5/00 433/216 |
| 2003/0057203 A1 * | 3/2003 | Seghatol | A61C 5/00 219/686 |
| 2003/0203339 A1 * | 10/2003 | Chilibeck | A61C 5/08 433/218 |
| 2007/0065780 A1 | 3/2007 | Dorsman et al. | |
| 2007/0141537 A1 | 6/2007 | Ibsen et al. | |
| 2007/0292821 A1 * | 12/2007 | De Vreese | A61C 5/00 433/195 |
| 2008/0081314 A9 | 4/2008 | Lazare | |
| 2008/0085493 A1 | 4/2008 | Sun et al. | |
| 2008/0090207 A1 * | 4/2008 | Rubbert | A61C 5/007 433/171 |
| 2008/0199826 A1 | 8/2008 | Jia et al. | |
| 2008/0299510 A1 | 12/2008 | Penchas et al. | |
| 2010/0297585 A1 * | 11/2010 | Yarovesky | A61C 5/10 433/199.1 |
| 2012/0065756 A1 * | 3/2012 | Rubbert | A61C 5/007 700/98 |
| 2012/0315601 A1 | 12/2012 | Shchori et al. | |

OTHER PUBLICATIONS

Amit Khatri, Lecturer, Department of Paedodontics and Preventive Dedntistry, UCMS & GTB Hospital; Delhi, India; 2010; vol. 1; Issue 4; pp. 288-290.

Jeff T. Blank, DMD; Direct Composite Veneers in Minutes, Not Hours: A simplified Technique and Material; Jun. 1, 2007.

Martin B. Goldstein, DMD, Template-Assisted Direct Composite Veneers; Feb. 1, 2010.

Frank J. Milnar, DDS,AAACD, The Evolution of direct Composites; Jan./Feb. 2011.

J.L. Ferracane, Current Trends in Dental Composites; Critical Reviews in Oral Biology & Medicine; Jan. 1, 1995.

Brigitte Zimmerli, Composite Materials: Composition, Properties and Clinical Applications; Nov. 2010, vol. 120.

Martin S. Spiller, DoctorSpiller.com; Composite Characteristics; The Criteria Dentists Use to Evaluate the Composites.

Martin S. Spiller, DoctorSpiller.com; Types of Composites; Types of Resin Composites.

Luis Guilherme Sensi, DDS, MS, PhD, et al., Direct composite Resins; Jul./Aug. 2007, vol. 3, Issue 7.

Kim JW, Kim LU, Kim CK, Cho BH, Kim OY, Charcteristics of novel dental composites containing 2,2-bis[4-(2-methoxy-3-methacryloyloxy propoxy) phenyl] propane as a base resin.

Robert Margeas, DDS; Long Lasting Multishade Composite Restorations; Feb. 14, 2013.

Dr. Eloy Burga Noriega, DDS, Creating a New Smile with your Own Hands; Direct Resin Veneers.

Dr. Thomas Trinkner, Dental Products Report: How to: Provide Veneers on a Budget; Nov. 2011.

A Solution for Everyday Direct Restorative Challenges; Journal of Cosmetic Dentistry, Fall 2010, vol. 26. No. 3.

Fahl, Junior N., The direct/indirect composite resin veneers: a case report; Pract Periodontics Aesthet Dent., Sep. 1996.

Ross W. Nash, DDS, The Direct Composite Resin Veneer: A Conservative Approach to Elective Esthetics.

Dr. Harvey Silverman, Cosmetic Dentistry:The Same Day Smile Makeover, Dental Products Report, Apr. 18, 2012.

Dr. Harvey Silverman, Same Day Smile Makeover: Selecting the right patients, Dental Products Report, Jun. 25, 2012.

Dr. Harvey Silverman, Cosmetic Dentistry: The Same Day Smile Makeover, Part 3, Dental Products Report, Sep. 19, 2012.

Cramer, N.B., et al., Recent Advances and Developments in Composite Dental Restorative Materials, Journal of Dental Research, Apr. 2011.

\* cited by examiner

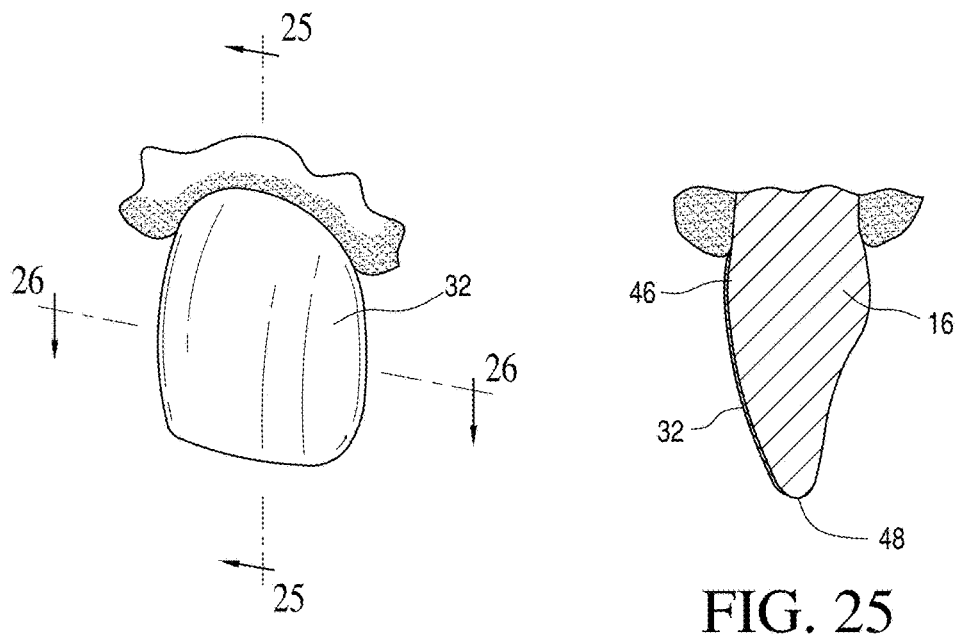
FIG. 24
FIG. 25
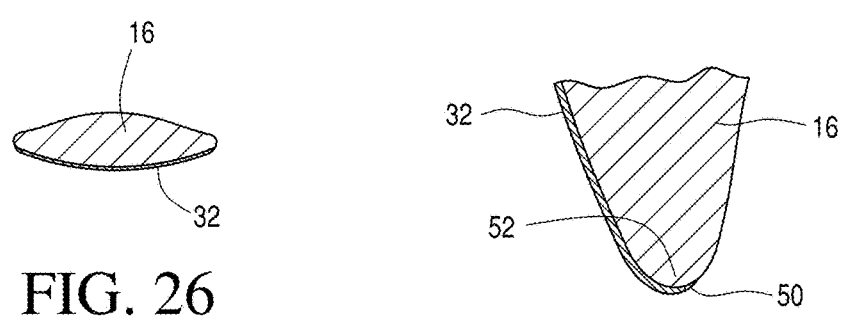
FIG. 26
FIG. 27

NON-INVASIVE METHOD OF MAKING A TOOTH VENEER

RELATED APPLICATIONS

This is a nonprovisional application of provisional applications Ser. No. 61/810,989, filed Apr. 11, 2013, and Ser. No. 61/863,250, filed Aug. 7, 2013, both of which are hereby incorporated by reference and the priority benefit of both are hereby claimed.

FIELD OF THE INVENTION

The present invention relates generally to cosmetic dentistry, including aesthetic dental procedures and general restorative procedures performed in the dental office and particularly to tooth modification, enhancement and alteration using non-invasive veneers.

BACKGROUND OF THE INVENTION

White, straight, even teeth are widely regarded as cosmetically attractive and desirable, both in the United States and in numerous other countries. It conveys health, beauty, success and happiness. A friendly, beaming, self-confident smile shares an instant non-spoken universal message with whomever one meets. However, the size, shape and color of teeth can be adversely affected over time by activities including eating, drinking, smoking, sports, accidents, nighttime bruxism and so forth. Other individuals have a variety of dental needs that require aesthetic restoration of the teeth due to spaces, chips, malformed or misshaped teeth, uneven or crooked teeth as well as a myriad of other aesthetic dental problems. Treatment has typically required expensive and extensive dental work that can often result in dental veneers that don't look natural and tend to look like the individual had their teeth "fixed". Accordingly, there is a need for a method of making tooth veneers that eliminates the time, expense, loss of control of the size, shape and illusions that can create a natural looking smile or an artificial appearance that many consumers want to avoid after having their teeth treated.

Some tooth veneer techniques employ the use of a porcelain restoration that can make teeth appear too large, wide or do not match the shade of the consumer's adjacent teeth. The size and shape of the veneers also often do not blend in well with the shape of the consumer's face. All of these factors help create veneers that look unnatural and are considered to be undesirable to the average consumer who wants to have a natural looking smile. Conventional porcelain veneer technology requires the experience of a skilled practitioner to perform one or more of the following to have a dental laboratory fabricate a porcelain veneer that can be bonded to the facial (front) surface of the teeth: initial consultation, written smile analysis, chairside smile analysis, taking study models, wax ups, tooth preparation, local anesthesia, impressions, face bow transfer, temporaries, dental indexes, try in appointments, shade and veneer modification, finishing and polishing as well as other procedural steps. This can be time consuming and very expensive. The tooth preparation can be minimal to significant depending on the requirements of the patient's dental aesthetic condition as well as the philosophy and technique employed by the laboratory technician in creating a porcelain veneer. Some dentists employ tooth preparation techniques that require so much tooth preparation that the dentist needs to fabricate temporary veneers for the patient to wear until the final porcelain veneers are completed. Otherwise the teeth would be exposed to temperature changes in the oral cavity causing sensitivity as well as creating an unaesthetic appearance when the patient would be in public. All of these steps contribute to high fees that make veneer systems affordable to a select few. Fees can be so high that the average consumer who could benefit from veneer technology is unable to afford these services. Thus, a need exists for a method of making tooth veneers that eliminates the requirement of tooth preparation as well as the time and expense associated with all of the additional requisite steps employed by dental professionals skilled in the art and science of restoring teeth using porcelain veneers.

As part of the fabrication process, conventional porcelain veneers are also etched by the laboratory technician for enhanced retention and are later bonded by the dentist to the facial surface of the teeth using a bonding agent, typically made of a composite resin. When a dentist tries in the porcelain veneer and uses a try in paste to hold the veneer onto the tooth, the dentist must make certain that the micro-porosities created by the laboratory technician when etching the inside of the veneer are not compromised during the try in phase or retention will be compromised, resulting in a delaminated veneer. If the veneer does not match the size, shape color or appearance of the adjacent teeth, or if a laboratory technician was unable to create the appropriate illusion effects with the porcelain veneer to match the size, shape and overall appearance of the patient's smile line and facial shape, then additional try in appointments will be required. This increases the patient's stress level as well as the dentists, not knowing how the final veneer will look. Thus, a need exists for a method of making tooth veneers that can easily be fabricated, tried in and adjusted by the dentist, allowing the dentist to control factors such as size, shape, color and illusion affects with the veneer and then to bond the veneer that same day to the patient's teeth once the dentist and patient agree on the aesthetic appearance, in one appointment, thus saving the patient time, expense and enhances the final aesthetic outcome.

A perceived advantage of porcelain veneer systems are that porcelain baked in an oven obtains high luster and resists staining. However, the final outcome of how a porcelain veneer will look in the patient's mouth can only be approximated by the dentist who either uses a best guess scenario or attempts to determine the final appearance of the veneer with the use of computer imaging systems. This can present a very real problem for patients when the dentist and laboratory technician are unable to deliver a veneer that matches the imaging produced by the computer system. This is because computers are unable to drill and prepare the teeth and thus, the computer imaging software can estimate what the final outcome might look like. The dentist's skill set and technical ability may or might not match what the computer imaging system anticipated the final outcome would look like when it is the dentist, and not the computer, who has to replicate and duplicate what the computer imaging system hoped for as a final result. Thus, a need exists for a method of making tooth veneers that provides patients with a more predictable outcome using composite resin technology that can enhance the patient's dental appearance while providing the patient with an outcome that matches the anticipated results.

For the porcelain veneer, since the laboratory technician is typically not in the dental office, the technician is not able to see how light reflects off the porcelain surface once placed on the patient's tooth. Thus, for example, when a patient wants to close a diastema (space between the teeth), the laboratory technician might produce an anatomically correct veneer that once tried in the mouth does not fit the patient's smile since the laboratory technician does not have the ability to see how light reflections bounce off the teeth. This effect might make the veneers that closed the space look unnaturally wide for that patient. Thus a need exists for a method of making tooth veneers that allows the dentist to control the light reflections in order for the veneer to minimize, if not completely eliminate, the issue of size and shape concerns.

Every dentist knows that the most difficult procedure to do is a single veneer to match the adjacent teeth. This is because teeth often have subtle color differences from one tooth to the next, making it very challenging, if not impossible, to have a laboratory technician match these shade variations when fabricating a veneer in the dental laboratory. Since the laboratory technician is typically off premises and working in a dental laboratory with a written work order and maybe a picture from the dentist, the laboratory technician can only guess at how the veneer might blend in with the adjacent teeth. Additionally, when a single veneer is done, it often adds more bulk to the teeth than the adjacent teeth and creates an aesthetic dilemma for the dentist and patient when the tooth tends to "stick out". Thus, a need exists for a method of making tooth veneers that allows the dentist to closely match the size, shape and color of the adjacent teeth with the dentist having in-office control of these factors to achieve a more predictable, aesthetically pleasing match to the adjacent teeth.

Problematically, other conventional veneer systems such as composite resins do not provide the patient or dentist with an exact preview of how their veneer will look and can often appear large, bulky and can absorb stains that mar the appearance of the final veneer. Still further, in some subjects gum irritation is induced in some patients by the composite veneer process, sometimes to the point of causing gingivitis or other periodontal issues. Thus, a need exists for a method of making tooth veneers that allows the dentist to avoid gum irritation, bulkiness, resist staining and plaque accumulation.

Conventional composite veneers also require the dentist to have the artistic ability to sculpt the veneer directly on the patient's teeth. Since this takes significant effort and expertise, most dentists prefer to do what they were initially trained to do in dental school, to pick up a drill and prepare, or "file" the tooth down, requiring the removal of otherwise healthy enamel, and then to take an impression and hope that the dental laboratory is able to produce a veneer that is satisfactory and pleasing to the patient. However, this may not always be in the patient's best interest to have healthy tooth enamel removed. It may also not be in the patient's best interest since the patient may be unable to afford the high fees associated with porcelain veneers. Further, the laboratory technician in making the porcelain veneers can only anticipate what the dentist will be seeing when trying the veneers on the patient at the office and consequently creates a veneer that may or may not look as natural or matches the size, shape or color as the patient wants. Thus, a need exists for a method of making tooth veneers where a veneer can be created in an office setting where a dentist can have complete control of the variables that create a beautiful, natural looking veneer.

Conventional composite veneers are typically done with the patient in a reclined position and the dentist applies tooth colored resins in a layered manner to correct the aesthetic problem that the patient wants to improve. However, this conventional technique does not allow the dentist or patient to know in advance just what the final veneer will look like. This fosters an uncertain outcome and causes a scenario where patient's expectations may not be met or requires multiple follow up visits to achieve what the patient had in mind. With repeated effort and a degree of luck, the layered composite veneer might be pleasing and satisfactory to the patient. Without such luck, the dentist may have to modify or possibly redo the veneer until the patient is satisfied. Thus, a need exists for a method of making tooth veneers that allows the dentist using in-office restorative materials, such as conventional composites, to accurately demonstrate and then reproduce what the patient desires, shaped and characterized to meet their personal expectations.

Conventional composite veneers also are difficult and laborious to perform from the dental practitioner's perspective. It can take significant amount of in-office time to mold and sculpt a veneer, precious time that the dentist may not have. Some in-office conventional composite veneer techniques can take up to several hours, if not longer, to treat just one patient who may have multiple teeth that require aesthetic enhancement. When the patient is shown the final result, the patient may need to return for additional contouring and shaping appointments in order for the veneer to aesthetically blend in with the adjacent teeth. All of this creates a dilemma for dentists who either do not have the time to block off several hours to perform the initial aesthetic transformation or who may not have the artistic talent to create a veneer that utilizes the principles of size, shape and color to create illusions, resulting in beautiful veneers that provide predictable, long lasting, outstanding aesthetic results. Thus a need exists for a method of making tooth veneers that helps simplify the material application skills, creates a beautiful looking veneer in one visit in a shorter period of time and decreases finishing and polishing time and minimizes the number of visits required to achieve a bright, dazzling, engaging smile.

Conventional composite veneers are often made by a dentist after doing computer imaging or wax mock-ups on a study model. However the dentist or patient does not know if the results achieved on a computer or on a study model can be replicated in the patient's mouth. After the dentist places and washes off an etchant on the tooth the dentist will then place and cure a bonding agent on the tooth's surface. A composite of choice is then placed on the tooth. Many dental manufacturers recommend placing an opaque layer on top of the cured bonding agent and/or using tinting agents to help neutralize any discolorations on or inside the tooth that could show through the composite restoration. This requires additional chair time and knowledge of how to use these agents in a manner that does not create an artificial appearance. For the general dentist this is a skill set that is not known as it requires an artistic basis in contrast to the restorative background dentists are trained in. After the process of neutralization is achieved, many dental manufacturers recommend placing a body or dentin layer of composite material on the tooth's surface. After the body layer is selected the dentist then needs to select an enamel layer that is placed over the dentin layer. Some manufacturers also recommend placing an incisal shade of composite over the biting edge of the tooth. The time and aesthetic skill required to perform these tasks is beyond the skill set that the general dentist has cultivated in their practice and thus, the dentist looks to the laboratory technician to provide them with porcelain veneers. Thus, there is a need for a method of making tooth veneers that eliminates the majority of the above referenced procedural steps to provide their patients with a noninvasive, cost-effective solution to correcting the size, shape or appearance of one or more teeth.

Tooth preparation for porcelain veneers typically require enamel removal along the facial (front), incisal (biting edge) and interproximal (sides) surfaces of the tooth. Removal of the incisal edge concurrently removes some of the lingual surface. The prep technique associated with porcelain veneers is still essentially a relatively invasive dental procedure, requiring the destruction of healthy tooth structure even when there is no overlapping, crowding or malpositioning of teeth. The processes are uncomfortable and relatively expensive for the patient. Thus, there is a need for a method of making tooth veneers without the invasive tooth preparations that prior art veneers require.

SUMMARY OF THE INVENTION

The present invention provides a non-invasive method for making a tooth veneer from composite resin material for a patient's tooth without tooth reduction, enamel removal or any invasive tooth preparation, comprising the steps of:

a) transferring an amount composite resin material on the patient's tooth without prior invasive tooth preparation;

b) forming a preview veneer from the composite resin material directly on the tooth;

c) requesting the patient to approve or disapprove the preview veneer;

d) if approved, requesting the patient whether to have a first method veneer or a second method veneer;

e) if the patient chooses the first method veneer, removing the preview veneer; and f) bonding the preview veneer to the tooth.

The present invention also provides a non-invasive method for making a tooth veneer from composite resin material for a patient's tooth without tooth reduction, enamel removal or any invasive tooth preparation, comprising the steps of:

a) transferring an amount composite resin material on the tooth without prior invasive tooth preparation;

b) forming a preview veneer from the composite resin material directly on the tooth;

c) requesting the patient to approve the preview veneer;

d) if approved, requesting the patient whether to have a first method veneer or a second method veneer;

e) if the patient chooses the second method veneer, removing the preview veneer;

e) etching the tooth;

g) applying a bonding agent on the tooth;

h) transferring an amount of composite resin material on the tooth; and i) forming a veneer from the composite resin material directly on the tooth.

The present invention further provides a kit for a non-invasive method of making a tooth veneer for a patient's tooth without tooth reduction, enamel removal or any invasive tooth preparation, comprising:

a) a first container containing a composite resin material of sufficient quantity for forming at least one veneer directly on a patient's tooth;

b) a second container containing an etchant for etching the tooth designated to receive a veneer; and c) a third container containing a bonding agent for providing a surface on the patient's tooth to which the composite resin material is bonded.

BRIEF DESCRIPTION OF THE DRAWINGS

FIG. 24 shows a perspective view of a tooth with a single layer veneer made from composite resin material using the method of the present invention.

FIG. 25 is a cross-sectional view of the tooth and the veneer along line 25-25 in FIG. 24.

FIG. 26 is a cross-sectional view along line 25-25 in FIG. 24.

FIG. 27 is an enlarged cross-sectional view similar to FIG. 25, showing a rest stop.

DETAILED DESCRIPTION OF THE INVENTION

Figure 1:
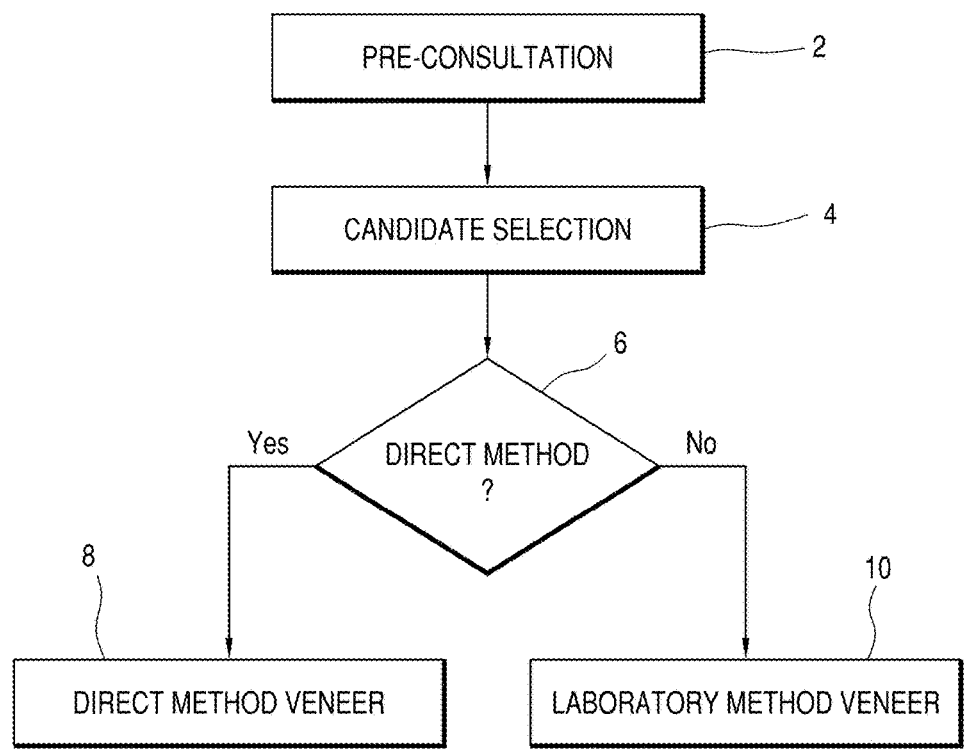
FIG. 1 is a flowchart of a non-invasive process for forming a single layer veneer on a tooth from a composite resin material in accordance with the present invention.

Referring to FIG. 1, a non-invasive method of making a tooth veneer is disclosed herein. The method includes a pre-consultation process 2, a candidate selection process 4, a direct method 8 and a laboratory processed method 10.

In the pre-consultation process 2, as will be further described below, the patient, after sending photographs of her teeth to the dentist, consults with the dentist on the telephone, if she would be a suitable candidate for veneers.

Once the patient is determined to be a candidate based on the pre-consultation process, the patient is asked to come.

In the candidate selection process 4, as will be further described below, the dentist makes a contact lens thin preview veneer directly on the patient's tooth without invasive tooth preparation, such as tooth reduction, enamel removal, drilling, etc. The patient is then asked if the preview veneer meets her approval. Once approved, the patient decides at 6 whether to get a permanent veneer by the direct method at 8 or the laboratory method at 10.

Pre-Consultation Process

The pre-consultation process saves a potential patient from unnecessarily traveling to the dentist office in case she is not a suitable candidate for veneers. If a patient will be traveling a long distance to his dentist or is hesitant about coming to the office for the initial consultation, the pre-consultation process allows the dentist to analyze the patient's smile through photographs that the patient would have previously sent and discuss with the patient by phone whether she would be a suitable candidate for veneers. The patient is asked to take the following photos and send them to the dentist via email or other means.

Figure 2:
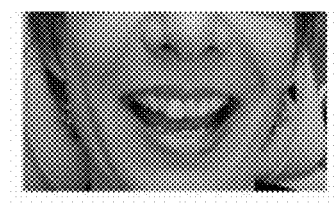
FIGS. 2-6 show pictures of a patient's teeth at various angles and teeth position.

A full face photo taken straight on with the upper and lower teeth slightly apart, as shown in FIG. 2.

Figure 3:
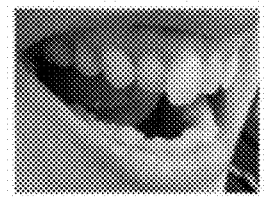
Figure 4:
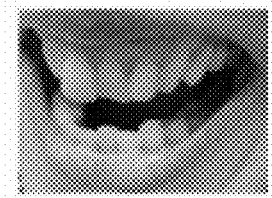

A medium close-up photo of the side view of the teeth open wide, on both sides, as shown in FIGS. 3 and 4.

Figure 5:
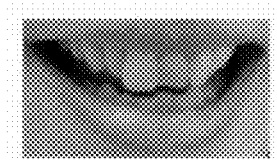

A medium close-up photo taken straight on with the teeth slightly apart and your lips making almost a rectangle, showing as much gum tissue as possible, as shown in FIG. 5.

Figure 6:
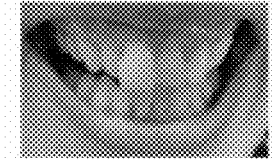

A medium close-up photo taken straight on of the front teeth after first biting on the back teeth and then sliding the lower front teeth until the biting edges of the upper and lower front teeth are touching edge-to-edge, as shown in FIG. 6.

The dentist looks for potential hazards that might be in the way of giving the patient a veneer. The dentist will look for signs of bruxism and carefully check the patient's occlusion, especially with regard to lateral excursions and protrusive interferences.

After reviewing the photos, the dentist will call the patient and ask a few questions about what the patient is looking to change about his/her smile. The patient can then make an appointment to see the dentist if it is determined that he/she may be a candidate for veneers. If the dentist can see potential problems, then the dentist can also visualize how to avoid them—and if there is no way, then the patient is informed that she is not a candidate for a non-invasive veneering procedure of the present invention before the dentist takes on the case.

Candidate Selection Process

Once the patient is determined to be candidate based on the pre-consultation process, a contact lens thin preview veneer will then be made for the patient's approval before the permanent veneer is made. The method of making a preview veneer and obtaining the patient's approval before making the permanent veneer determines whether the patient may or may not be a candidate for non-invasive or minimally invasive cosmetic dentistry using composite veneers made in accordance with the present invention. This process provides an actual pre-determined result without using computer imaging. After checking the patient's dental and periodontal health and eliminating potential candidates who need restorative treatment, the dentist will perform the following:

Step 1—The patient is handed a mirror and asked to look into the mirror and show the dentist which tooth or teeth the patient would like to correct, fix, change or enhance. This could relate to the size, shape, position in the dental arch, correction of chips, spaces between teeth or anything to do with the appearance, color or impact the tooth has when the patient talks, smiles or otherwise is not pleased with or is self-conscious about.

Step 2—A before photo is taken of the tooth or teeth the patient would like to change. A full face and medium close up picture (focusing on the lips and the teeth that show when the patient smiles) as well as a close up photo of only the teeth and gum tissue are taken. Photos with the teeth gently closed as well as with the teeth slightly apart so the dentist can accurately assess all aspects of the patient's cosmetic dental needs, including any spaces that exist between the teeth are also taken.

Step 3—The patient's occlusion is checked to make certain that there is sufficient room to place the veneer with the patient biting in centric, protrusive and lateral excursion.

Step 4—The patient is again given a hand held mirror as the dentist creates a veneer directly on the patient's tooth using a composite resin, which is also referred to as foundation material. The patient is informed that the dentist will now determine if a veneer can be custom made to solve the patient's dental problem while blending in with the color and appearance of the patient's adjacent teeth. The patient may choose to watch the dentist custom make the veneer to perfectly fit the tooth/teeth that the patient desires to enhance. The dentist will also select a shade of the composite resin 12. The dentist may choose to use the VitaPan Classical Shade Guide when doing shade selection (Vita is a registered trademark of the VITA ZAHNFRABIK, H. Rauter Gmbh & KG Bad Saeckingen, Germany). It is preferable to select a shade while the patient's teeth are moist. At this stage, the patient may also want their teeth whitened, in which case the method for tooth whitening described below will be used.

Step 5—The dentist will then dry the tooth with a cotton roll or gauze or by using a gentle stream of air from an air syringe. While drying the tooth is not imperative, it is advantageous in helping the foundation material 12 stay in place on the tooth. Once the foundation material 12 is light cured, the resulting structure is now referred to as a veneer.

Step 6—The dentist may choose to trans-illuminate the teeth with a composite curing light, such as for example Elipar™ S10 Curing Light by 3M, Spectrum 800 by Dentsply, etc. to determine if the patient's teeth to be treated have any previously placed composite material. If any composite material is detected, either visually or by observation with the trans-illumination, a separating medium would preferably be used to prevent the inadvertent splinting of the new veneer to the existing composite. For example, petroleum jelly placed over the existing composite in a very thin layer is an acceptable separating medium.

Step 7—Prior to placing the foundation material 12 on the tooth the dentist will evaluate access to the patient's teeth. For example, if the patients' size or positioning of their lips hinder good access to the teeth in question or prevents proper isolation of the teeth from the oral cavity, the dentist will place cotton rolls under the lips. This will provide unencumbered access to the teeth. Another option would be to place lip/cheek retractors, such as for example EXTND by Plasdent or Optragate by Ivolclar Vivadent, between the lips and teeth to gain access to the patient's teeth. By doing this the lips will not interfere with the placement of the foundation material 12 on the teeth.

Figure 7:
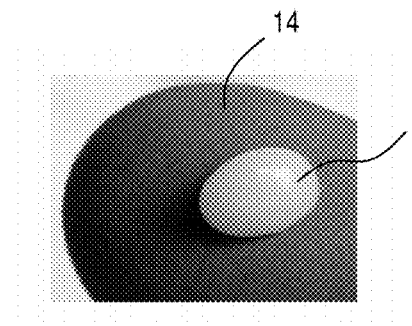
FIG. 7 shows a proper amount of composite resin material on a gloved finger to do a tooth after having been compressed or condensed to remove any air bubbles.

Step 8—The dentist will then syringe the foundation material 12 to be used in creating the veneer directly onto a gloved finger 14, preferably the index or middle finger, as shown in FIG. 7. Using a gloved thumb on the same hand or using a gloved finger from the other hand, the foundation material 12 is compressed or condensed into a ball-like shape, to remove any air bubbles, as shown in FIG. 7. The amount of the composite resin material 12 after being condensed in the ball-like shape is preferably about 5 mm in diameter to minimize overbulking when applied to the tooth.

The foundation material 12 is preferably a composite resin with high viscosity so that it is not flowable. The foundation material 12 is preferably condensable and non-sticky so the dentist can condense the composite resin between gloved fingers and move the material on the tooth without sticking to the dentist's gloved finger or instrument, but will stick to the tooth. The composite resin 12 has high viscosity (packable composite) as opposed to low viscosity (flowable composites). The composite resin 12 is workable enough to form a shape on the facial surface of the tooth fairly easily, but does not slump too much. The high viscosity of the composite resin 12 is such that the dentist is able to have sufficient control of the placement of the material once it is applied to the tooth. The composite resin 12 is advantageously easy to apply and sculpt. High viscosity and non-sticky properties of composite resins are well understood terms in the field of dental composites. The composite resin 12 is variously called dental composites, composite dental restorative materials, and direct composite resins in the dental literature. The composite resin material 12 preferably includes an optical refractive index that would prevent the inadvertent exposure of any discolored tooth structure immediately underneath the veneer. Examples of the composite resin 12 are Esthet X by Dentsply/Caulk, Filtek™ Supreme by 3M, TPH3 by Dentsply/Caulk, PROFIL™ Micro Hybrid Composite Resin by Silmet Ltd., www.silmetdental.com, etc.

Step 9—If the dentist has an overhead light that is turned on and directed at the patient's oral cavity, it is preferable for the light to be turned off to prevent premature curing of the foundation material.

Step 10—While the veneer can be created with the dentist in standing or sitting position, it is preferable for the dentist to be standing when creating the veneer. From a standing position, the dentist can accurately determine how light reflections alter the foundation material appearance on the tooth and thus, allows the dentist to create a more natural looking veneer. However, the dentist can also apply the foundation material on the tooth while in a sitting position but would need to evaluate the patient once the patient is sitting up. Evaluating the appearance of the veneer (or any composite veneer) is preferably made with the patient sitting in an upright position as it allows both the dentist and patient an opportunity to see how the veneer looks when other people interact with the patient—talking face to face while in an upright position.

Figure 8:
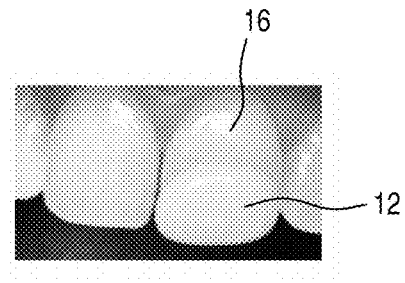
FIG. 8 shows the composite resin material in FIG. 7 after being applied to an incisal half of a patient's tooth.

Step 11—The foundation material 12 will then be placed on the isolated tooth 16 that the patient wants to cosmetically enhance, as shown in FIG. 8. The foundation material 12 may be applied by one of the following: a) the foundation material 12 is placed directly on the tooth 16 with the gloved finger 14; b) the foundation material is placed on a polyethylene pad or a similar pad and then transferred to a dental instrument of choice and then placed directly on the tooth; c) the foundation material is transferred directly from the gloved finger directly onto a dental instrument of choice, such as for example a plastic instrument by Hu Friedy, and then transferred from the plastic instrument to the facial surface of the teeth to be treated.

Figure 9:
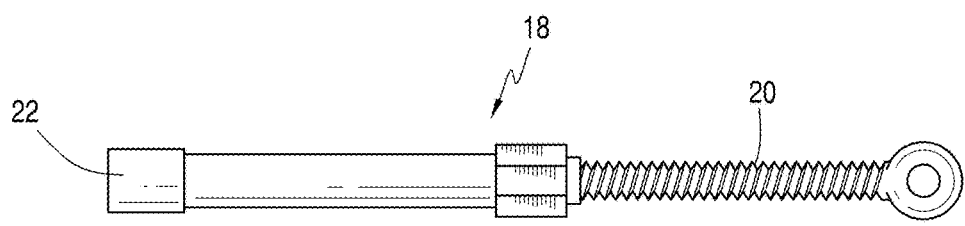
FIG. 9 is an exemplary composite resin dispenser.

Step 12—When dispensing the foundation material onto the gloved finger, it is preferable to dispense as small amount of foundation material as possible to advantageously prevent bulk of material from accumulating over the facial surface of the tooth while creating a contact lens thin veneer over the facial surface of the teeth. Referring to FIG. 9, for purposes of example, if the dentist is using a standard composite syringe 18, such as provided by Silmet with its PROFIL™ Micro Hybrid Composite Resin, or Filtek™ Supreme by 3M, TPH3 by Dentsply/Caulk, etc., a turn of one half a rotation on the syringe handle 20 should be sufficient to obtain sufficient foundation material for creating a contact lens thin veneer. However, the dentist may choose to turn the handle less to obtain foundation material for smaller teeth or turn the handle more than ½ of a turn for larger tooth. The suggested half-turn is based upon the composite resin material being flush at the syringe tube orifice. When taking off the cap 22 of a composite syringe 18, if composite material is not at the orifice of the syringe, the handle is turned until the composite material is at the orifice of the syringe tip. If the dentist is not using a syringe filled with composite material but is using a compule filled with the composite material, the dentist should only need to express approximately one third of the compule content to create the contact lens thin veneer.

Step 13—If a dentist expresses more material than desired, the dentist should take the foundation material off of the facial surface of the tooth and place it on a gloved finger or a polyethylene pad. Using a plastic instrument the dentist can then remove a percentage of the foundation material (e.g., one fourth of the foundation material if slightly over-bulked to one half or three fourths of material if significantly over-bulked). After the excess foundation material is removed, the dentist will then place the desired amount of foundation material back on the facial surface of the tooth.

Step 14—Next the dentist will shape the foundation material on the patient's tooth, as shown in FIGS. 8 and 10-13. When doing this it is preferable to control the appearance of the tooth being formed by considering the impact light reflections make on the tooth. By slightly moving the foundation material 12 in one direction or the other, the interaction of light with the foundation material will alter the perceived size, shape or appearance of the resultant veneer. For example, if the dentist moves the foundation material toward the incisal edge, the tooth will appear longer. If the dentist moves the foundation material away from the incisal edge so that light reflects away from the biting edge of the tooth, the tooth will appear shorter. The same is true when moving the foundation material toward or away from the interproximal surface. Moving the material toward the interproximal surface will make the tooth appear wider. Moving the material away from the interproximal surface will make the tooth appear narrower.

Step 15—One method to determine how light affects the appearance of the veneer is to place the foundation material on the middle of the facial surface of the tooth. Using a gloved finger or a plastic instrument the dentist can then move the foundation material toward the incisal edge of the patient's tooth. Once the dentist reaches the incisal edge care should be taken to ensure that no excess foundation material wraps around the incisal edge. Using a gloved finger or a plastic instrument, the excess material is gently removed from the lingual surface where inadvertent foundation material may have been placed. If this material is not removed and the dentist cures the foundation material using a curing light, then the veneer will likely crack into pieces upon removal at the end prior to proceeding to the direct method or laboratory method of making a permanent veneer, as will be described below. Cracking of the preview veneer is undesirable since the preview veneer can no longer be used to be bonded to the tooth, if the patient chooses the laboratory method as will be discussed below, after approval by the patient.

Step 16—Next the dentist will use a plastic instrument or a gloved finger to move the foundation material that remains on the middle of the facial surface and move and/or sculpt it toward the interproximal surfaces of the teeth, first toward the mesial and then toward the distal, or vice versa.

Figure 12:
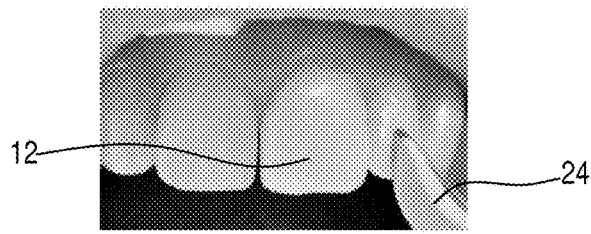

Step 17—Once the material has been sculpted over the facial surface of the tooth and now covers the top one-half of the tooth surface up to the biting edge and to the interproximal surfaces of the teeth, the dentist will take a thin bladed plastic instrument 24, such as for example a Goldfogel Instrument by Hu-Friedy and remove any excess material that contacts the adjacent teeth, as generally shown in FIG. 12. This will prevent any inadvertent splinting of the veneer to the adjacent teeth. While doing this the dentist is preferably in a standing position so light reflections from the room can be evaluated in determining the overall size, shape and appearance of the veneer. This also significantly eliminates interproximal finishing and polishing of the veneer after final cementation to the tooth.

Figure 10:
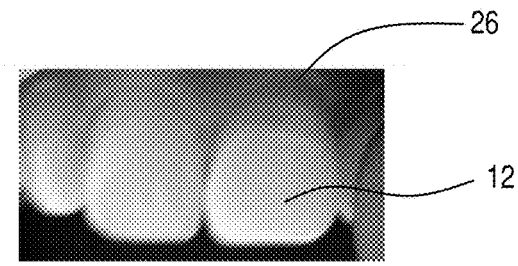
FIG. 10 shows the composite resin material after having been moved and spread toward the gingival surface of the tooth.
Figure 11:
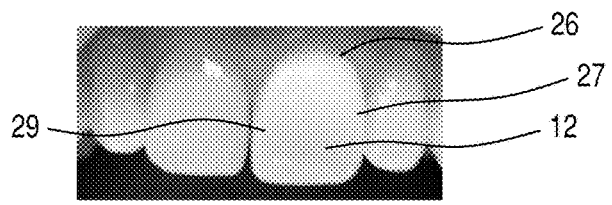
FIGS. 11-13 show forming the composite resin material on the patient's tooth.

Step 18—Next if enough material remains on the tooth, the dentist will sculpt the foundation material using a standard tool, such as a Goldfogel instrument, toward the gingival half of the tooth, gently moving the material toward the gum line 26 of the tooth, as shown generally in FIGS. 10 and 11, and the interproximal surfaces 27 and 29, as shown in FIG. 11.

Step 19—The dentist can add more foundation material to the gingival half of the tooth where the initial foundation material was placed as needed.

Step 20—In the above steps 14-18 after the foundation material has been placed on the tooth in steps 12-13, instead of moving the foundation material toward the incisal edge of the tooth, the dentist can also choose to first move the foundation material toward the interproximal or even the gingival of the teeth and then move the remaining foundation material to the other uncovered sections of the tooth.

Step 21—Once the dentist has enough foundation material on the tooth, the dentist will sculpt the foundation material over the remaining tooth surface while making certain that the material on the interproximal surface does not contact the adjacent teeth. If the foundation material is in contact with the adjacent teeth, that portion of the foundation material will be gently removed by the dentist using a plastic instrument. Removing and contouring the material in this manner is still possible since the dentist has not yet cured the foundation material with exposure to light and the overhead light has also been turned off previously to prevent inadvertent curing.

Figure 13:
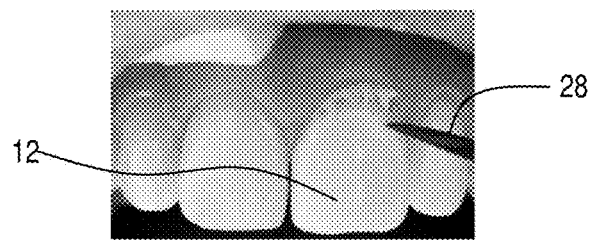

Step 22—To minimize the need to do extensive shaping, finishing and polishing of the composite veneer (which is customary with composite veneers) and to prevent bulk of composite accumulating by the gum tissue, the dentist will use a standard plastic instrument 28 or a scalpel, if so desired, to remove any bulk thickness of foundation material at the gum line where the veneer and natural tooth meet, as generally shown in FIG. 13. This process facilitates a seamless emergence profile between the root surface and veneer of the tooth, helping to maintain good periodontal health.

Step 23—Once the foundation material has been completely shaped over the tooth, the foundation material is now in the shape of a veneer. The dentist can look once again at the overall impact the foundation material creates and be certain that the shape of the foundation material along with the impact of light reflections will result in a veneer that looks natural in appearance while blending in with the size, shape and appearance of the patient's adjacent teeth. The dentist will also take one final look at the incisal edge of the tooth to avoid a facial-lingual lock from the foundation material that would cause the veneer to fracture in pieces upon removal after the veneer is cured as stated above (step 15). The dentist will also take one last look at the interproximal line angles created by the veneer to make certain that the veneer does not look too wide or narrow and to ensure that inadvertent splinting of the teeth will not occur once the veneer is cured with a dental curing light.

Figure 14:
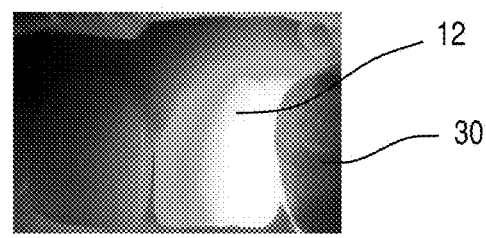
FIG. 14 shows a light source curing the composite resin material after it has been shaped and formed into a veneer.

Step 24—The dentist will then cure the foundation material with a light source 30, as shown in FIG. 14. The preferable curing technique for creating a veneer that will be fully cured and will not have any unexposed areas or that are under-cured is to cure the veneer in five segments; namely, the gingival, incisal, middle of the facial, distal and mesial. Each section should be exposed to light for a period of 10-20 seconds, based upon the manufacturer's directions. However depending on the manufacturer's instructions for the light curing unit, the dentist may need to increase or decrease the exposure time as well as the segmentation with respect to providing exposure of the foundation material to the light source.

Figure 15:
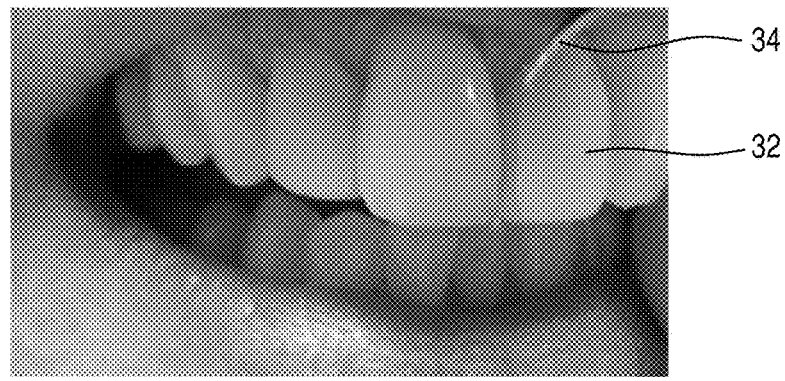
FIG. 15 shows removing the veneer from the patient's tooth.
Figure 16:
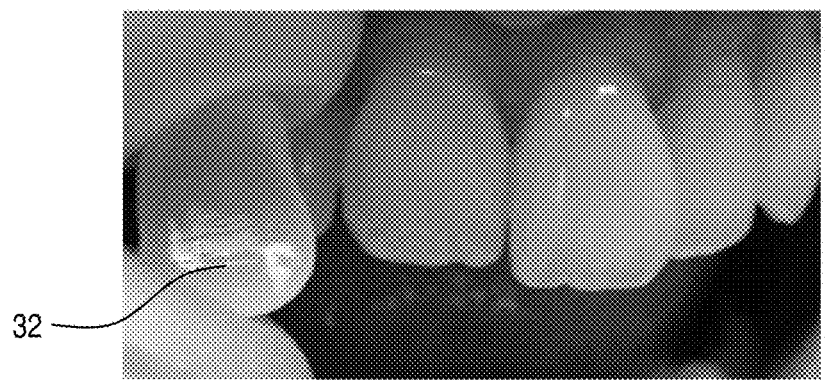
FIG. 16 shows the formed veneer after removal from the patient's tooth.

Step 25—Once the foundation material has been cured a preview veneer 32 has now been created, as shown in FIGS. 15 and 16. While sitting upright the patient should be given a mirror and asked to look at the transformation. The entire process to achieve all of the above typically takes 60-120 seconds from start to finish, excluding the light curing time.

Step 26—Along with patient, the dentist should look at the overall enhancement that was achieved. The preview veneer 32 should be evaluated to see if it looks natural, as if the patient was born with this tooth (e.g., veneer), whether it blends in with the adjacent teeth or if additional veneers might be necessary for symmetry purposes, whether any undesirable discolorations are showing through the veneer, and confirm that the color, size, shape and overall appearance of the veneer is what the dentist and the patient hoped to accomplish.

Step 27—Next the patient is asked look at the comparison of the before photo to her new smile created with the preview veneer. Using a digital camera or a digital tablet, the before photo can be shown to the patient next to her face while the patient is holding the mirror.

Step 28—After photos of the veneer are preferably taken using the same approach as suggested in step 2 above.

Step 29—The patient will now be shown the before and after photos that are on the digital camera. The patient can be reminded that these are the actual photos and that the transformation she witnessed is not computer generated but from the fabrication of the actual preview veneer that was custom made to her tooth. It is also suggested to inform the patient that the patient's actual tooth (no tooth reduction, enamel removal along the facial, incisal and interproximal reduction/drilling, reduction, etc. had been done to the tooth) is still under the veneer. When evaluating the transformation, it is best to hold a mirror at arm's length which is how other individuals will perceive the transformation at a social distance. The patient may also look at the transformation under close examination; however, it is always helpful to remember that the illusion created at a social distance is what photographs will capture and what friends and family typically notice.

Step 30—The patient will be asked to provide an honest assessment of the smile transformation. The patient can give a score of A, B, C, D or F based upon the expectations she had prior to coming to the office and what the dentist was able to accomplish. A, B, C, D and F is a standard scoring system used in grading students, A being the highest score and F being a failure and B, C and D falling in between the two extremes from high to low. The patient is instructed that being honest is essential since it is important for both the patient and the dentist to determine if the dentist's skill set with this particular technique matches her expectations and if it does not, this is the time to make that assessment. The dentist may also want to state that it is far better to decide that the preview veneer does not accomplish the patient's desire smile enhancement goal prior to doing the actual work since the preview veneer that was just made will provide the patient with a preview of how her final transformation will appear once the final veneer is made.

Step 31—If the patient provides an assessment of A or B, then the dentist can have the confidence to proceed with work to make the final veneer. A grade of C or below would not be a desirable outcome and it would be best not to do the cosmetic dentistry using composite veneer. An exception to a poor grade is that the dentist may want to do another preview veneer using a different shade of foundation material or use a foundation material from another manufacturer that has more or less opacity, etc., built into the foundation material that will create a better result.

Step 32—Proceeding with the final work after the transformation has been evaluated gives the patient the confidence that the results will meet her expectation since she made an honest assessment of what was accomplished prior to committing to having any work one.

Step 34—The preview veneer 32 will now be carefully removed. Since the veneer 32 is not bonded to the tooth at this point, the veneer will gently come off the tooth. The patient can touch it and see how thin, translucent and natural looking it is. The patient sees the a preview of the final result before committing to having any work done, since the preview veneer shows what the final veneer will look like. The patient sees firsthand what the dentist's cosmetic skill set and determines if that matches her level of expectation prior to having any work done. The dentist will remove the preview veneer by first looking at the lingual surface of the tooth and making certain that no foundation material (as stated in Step 15 above) flowed over the incisal edge of the tooth that would create a facial-lingual lock and possibly cause fracture of the veneer upon removal. If any foundation material is observed, it should be selectively removed until no material remains. The dentist can use a standard diamond bur of choice to selectively remove any inadvertent material from the lingual surface.

Step 35—The dentist will then select a dental instrument 34 such as a dental scaler, such as for example U15 by Hu-Friedy, and gently place the tip of the instrument under the gum line where the veneer and tooth meet, as shown in FIG. 15. The veneer is gently removed in one motion (using a removal force toward the incisal edge of the tooth) and if no facial-lingual lock exists, the veneer will come off as one piece.

Step 36—The dentist will place the preview veneer 32 between the gloved fingers, as shown in FIG. 16 and show it to the patient. The veneer is held on its side to show the patient how the veneer is contact lens thin.

Step 37—Next the dentist holds the veneer on its side with the shiny lingual side of the veneer facing the patient or vice versa. With the dentist's other hand place, the dentist places a gloved finger in front of the veneer to show the patient how the veneer is translucently thin, meaning that the gloved finger or a shadow of the finger will show through the thickness of the veneer on the other side. The translucency of the veneer is an important element in achieving natural looking teeth. The veneer is similar in thickness to a contact lens, which is generally about 0.09-0.16 mm in thick. Some veneers or dental crowns/bridgework use opaquers that often make the teeth look artificial, or as patients report, like "the teeth were fixed".

Step 38—By removing the preview veneer 32, the patient can also see that this is an actual veneer that was created by the dentist that was customized to the size, shape and appearance of the patient's adjacent teeth. No guesswork remains from the dentist or patient perspective relative to the final outcome or appearance of the veneer and whether the veneer will satisfy the patient.

Step 39—The dentist will then explain that if the patient wants to proceed, the patient can either have the direct technique or the laboratory method. If the patient does not want to proceed, then her tooth is still the same. No invasive tooth preparation procedures, such as tooth reduction, enamel removal, drilling, etc., had been done her tooth to make the preview veneer.

Laboratory Method

In the laboratory method, the preview veneer 32 will be reused and permanently bonded to the patient's tooth. After the patient has approved the size, shape, color and overall appearance of the composite veneer that was created during the preview process described above and prior to removal of the preview veneer 32, the dentist will preferably place a small amount of composite resin material over the incisal edge of the tooth to function as a positioning stop to make sure that the veneer is re-positioned at the original position when the veneer is bonded to the tooth. The incisal rest is placed directly on the veneer that covers either half of the biting surface of the tooth or even the entire biting surface of the tooth as long as there is absolutely no foundation material that wraps around and is placed on the lingual surface of the tooth—since that would create the labial-lingual lock that would cause fracturing of the veneer during removal of the veneer in the candidate selection process.

A standard positioning jig may also be used, using for example vinyl polysiloxane material such as Jet Bite by Coltene Whaledent or a bite registration material of choice, or using a thermoplastic material such as for example Bite-Buddy by All Dental Prodx, by taking an alginate impression of the veneers in place and pouring up a stone model from the cast made from the alginate impression and fabricating an incisal jig using a vacuum formed bleaching tray material of choice that would be placed over the veneers prior to curing the veneers with light after the bleaching tray is created in the laboratory. The vacuum formed bleaching tray is customized to the veneers by taking an impression of the teeth after the veneers are tried in and approved by the patient and a stone model would be poured and the clear vacuum formed tray would be created. Additional jigs can be made from other materials such as a positioning wax.

The dentist can also use a polyvinyl siloxane bite registration material that is placed over the labial surfaces of the teeth. After the bite registration material has cured the dentist would remove the composite veneer from the tooth using a dental scaler such as a U 15 by Hu-Friedy.

Other positioning devices include leaving a small button of composite on the middle of the incisal surface of the tooth that could be easily removed after placement of the final veneer on the etched tooth that has had a bonding agent applied to the surface of the tooth. When using this approach it is imperative that a labial-lingual lock is not created by wrapping too much composite veneer material over the incisal edge or the dentist will find that the veneer will fracture upon removal of the veneer from the tooth. To avoid the problem, an incisal positioning stop would be placed by the dentist after the patient has approved the veneer by placing a small amount of composite resin material which can be from 0.5 mm to 1 mm or greater over the incisal edge of the tooth.

Another option would be to reposition the veneer on the tooth and then intentionally place a lingual button of foundation material over the incisal edge of the tooth that would be cured and then removed upon final cementation.

Another alternative to the positioning jigs described above is the provision of one or two small rest stops placed on the patient's tooth to create positive seat rests (i.e., a rest stop) for the veneer. The patient would be told that these small rest stops are only ¼ to ½ mm in depth and would not necessitate filing down of the tooth—simply a minor alteration to facilitate seating of the veneer after the laboratory process has been completed. These rest stops can be placed on the facial surface of the tooth.

Figure 17:
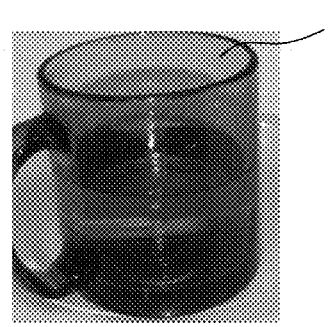
FIG. 17 shows a microwave-safe cup with water used to treat the veneer shown in FIG. 16 in a microwave oven.

The veneer 32 is treated in a microwave prior to cementing to the patient's tooth. Microwave treatment may provide enhanced resistance to staining, improved physical properties and is indicated for patients who consume more than 3 cups of coffee/tea per day or smoke cigars or cigarettes. It may also be useful with patients who prefer red wine, use a lot of soy sauce and for patients with significant bruxism. The veneer is placed in a microwave safe cup 36 containing water and heat treated in the microwave for about 3 minutes, as shown in FIG. 17.

After the inside surface of the veneer 32 is roughened by a diamond bur or micro-etched using a sand blaster such as for example Microetcher IIA Sandblaster by Danville (san Ramon, Calif.), the dentist will clean inside surface of the veneer with a 37% ortho-phosphoric acid, rinsed, and then prepped with a bonding agent, which is an unfilled resin, such as for example be Prime and Bond by Dentsply/Caulk, http://www.caulk.com/pages/products/Prime&Bond.html or Scotchbond by 3M, http://solutions.3m.com/wps/portal/3M/en_US/3M-ESPE-NA/dental-professionals/promotions/scotchbond-universal/. The etchant is applied to the inside surface of the veneer and thoroughly rinsed for 15-30 seconds and blotted dry with a cotton roll, gauze, etc. or gently dried with a stream of air from a syringe—such as an air water syringe. This is then followed by placing the bonding agent to the inside surface of the veneer. Prior to attaching the veneer to the tooth, a thin layer of composite luting material, which is a low viscosity flowable composite resin, such as for example Variolink Veneer by Ivoclar Vivadent, http://www.ivoclarvivadent.us/variolink/, or Mojo Veneer Cement, http://www.pentron.com/index.php/products/product_detail/mojo_veneer_cement, is applied to the inside surface of the veneer. The veneer, which now has the bonding agent and composite luting agent, is gently placed on the tooth.

Figure 18:
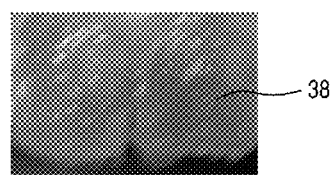
FIG. 18 shows the application of etchant on teeth on which veneers will be formed after the patient has approved the preview veneer shown in FIGS. 15 and 16.
Figure 19:
FIG. 19 shows the application of a bonding agent on the tooth after the etchant has been rinsed on the tooth on which a veneer will be attached or formed.

The tooth prior to attachment of the veneer is etched with an etchant 38 which is preferably 37% ortho phosphoric acid formulated to create microporosities in the tooth enamel, as generally shown in FIG. 18. After about 15-60 seconds, the etchant is rinsed with water and the tooth dried. After rinsing, a bonding agent, such as an unfilled resin liner is applied, as shown in FIG. 19. The unfilled resin liner provides a bonding surface on the tooth to which the veneer is attached. The unfilled resin liner is allowed to stand for about 30 seconds and the excess is removed with an air syringe. A thin layer of the unfilled resin is kept on the tooth. The unfilled resin liner is cured with a light for about 10-15 sections per section of the tooth exposed to the light source, such as for example the incisal, middle of the facial, gingival, mesial, distal and lingual sections. When curing, it is preferable not to underexpose or chipping of the veneer can occur due to poor bond strength of the veneer to the enamel of the tooth.

After the composite veneer is placed on the tooth and positioned using the rest stop or a jig, the dentist will then cure the gingival third of each composite veneer to be bonded to the teeth. Once the establishment of proper positioning has been established the dentist will then remove the jig, if used, and place dental floss through each contact area prior to the curing of the composite veneer. Any excess bonding resin cement will be removed with a dental explorer or dental instrument such as a dental scaler or plastic placement instrument. Once the excess cement is removed the dentist will expose all of the remaining surfaces of the composite veneer to a dental curing light for a period of time that sufficiently cures the underlying resin cement. In most cases this will typically be from 10 seconds to 20 seconds or more per portion of the composite veneer that is covered by the light but the exposure time may be shorter or longer depending on the manufacturer's instructions.

Figure 20:
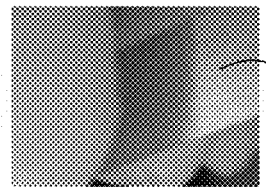
FIG. 20 shows an interproximal saw for removing any splinting caused by interproximal bonding material.

If any resin cement inadvertently bonds adjacent teeth together the dentist will separate the teeth using a separating saw 40, such as one made by Contact EZ (Vancouver, Wash.), as generally shown in FIG. 20. By placing the saw teeth in the incisal embrasure on either the mesial or distal of the teeth, the saw will gently open up the contact by pressing the saw in a gingival direction so the patient can floss and ensure optimum health.

Figure 21:
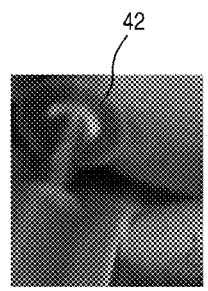
FIG. 21 shows a polishing disc for polishing the veneer on the patient's tooth.
Figure 22:
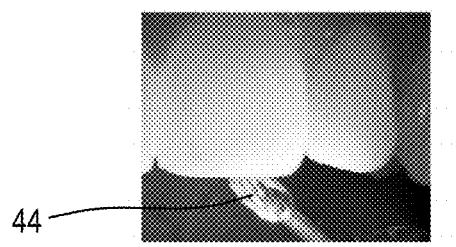
FIG. 22 shows the use of a finishing bur for removing any excess material on the cervical region of the veneer.
Figure 23:
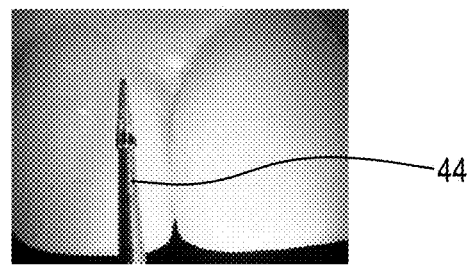
FIG. 23 shows the use of a finishing bur to insure a smooth transition between the veneer and the tooth in the gingival emergence profile.

Polishing disc 42 may be used lightly over the surface of the veneer, as shown in FIG. 21. Minimal time is expended in finishing and polishing on lingual surface with carbide finishing bur 44, as shown in FIG. 22 since excess foundation material has been removed prior to curing. A seamless emergence profile is made using the carbide finishing bur 44, as shown in FIG. 23.

Direct Method

If the patient decides to have the direct method after approving the preview veneer, the preview veneer 32 is then removed. An etchant is applied to the tooth that will receive a veneer, as generally shown in FIG. 18. The etchant is preferably 37% ortho phosphoric acid formulated to create microporosities in the tooth enamel prior to placing the bonding agent. After about 15-60 seconds, the etchant is rinsed with water. If two teeth are going to have the veneers, both teeth will be treated with the etchant.

After rinsing, an unfilled resin liner is applied, as generally shown in FIG. 19. The unfilled resin liner provides a bonding surface to the veneer. The unfilled resin liner is allowed to stand for about 30 seconds and the excess is removed with an air syringe. A thin layer of the unfilled resin is kept on the tooth. The unfilled resin liner is cured with a light for about 10-15 sections per section of the tooth exposed to the light source, such as for example the incisal, middle of the facial, gingival, mesial, distal and lingual sections. When curing, do not underexpose or chipping can occur due to poor bond strength of the veneer to the enamel of the tooth.

The permanent veneer is then created directly on the tooth, using the same steps as in creating the preview veneer.

Referring to FIGS. 24, 25 and 26, the completed preview veneer 32 is shown. The veneer 32 is advantageously translucently thin so that light passes through it in a translucent manner. The veneer 32 is similar in thickness to a contact lens. The thinness of the preview veneer 32 advantageously contributes to its appearance as being life-like. The veneer 32 has edge 46 that is advantageously feathered into the gingival surface of the tooth. Referring to FIG. 25, note that there is no veneer material on the incisal surface 48 of the tooth 16 to minimize the risk of the veneer 32 from cracking when removed, if the patient chooses the laboratory method.

Referring to FIG. 27, a portion 50 of the veneer 32 extends into the incisal surface of the tooth. The portion 50 is added is added to the veneer 32 prior to removal if the patient elects to have laboratory method. The portion 50 conforms to the shape of the incisal surface 52. The portion 50 functions as a rest stop that provides the dentist a guide to insure that the veneer 32 will be bonded to the tooth 16 at the exact position and orientation that the veneer occupied prior to its removal. After the veneer 32 is bonded to the tooth after the patient selects the laboratory method, the portion 50 may be removed or left behind. As discussed above, other ways of guiding the dentist to correctly reposition the veneer to its original position on the tooth after its removal may be used.

It should be understood that the veneer 32 may also represent the direct method veneer without the portion 50 or the laboratory method veneer.

Figure 28:
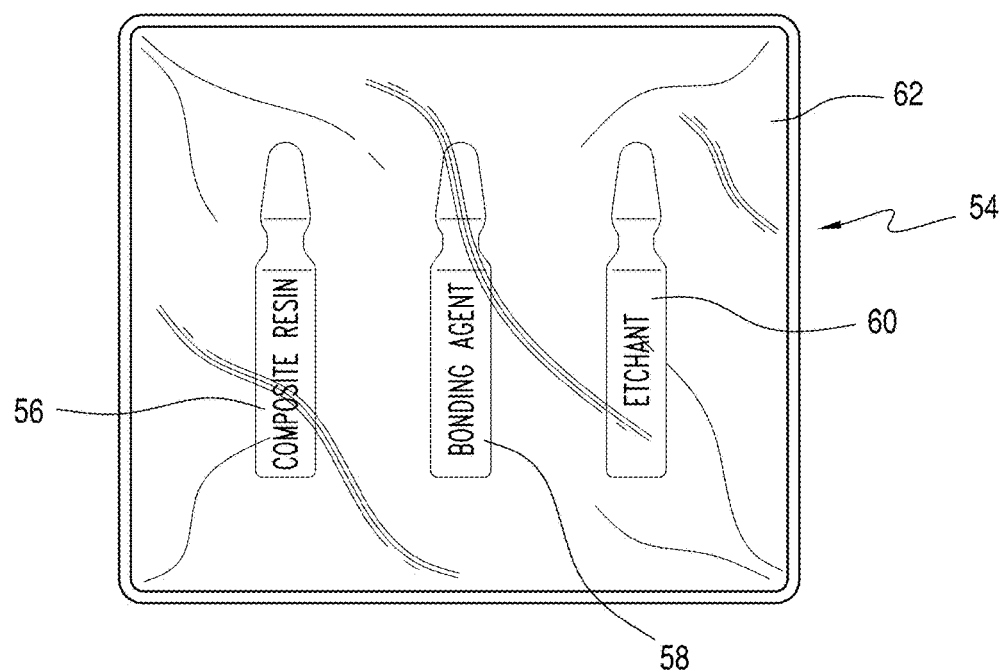
FIG. 28 is a schematic front view of a kit containing a composite resin material, an etchant and a bonding agent of sufficient amount to form at least one veneer on a tooth using the method of the present invention.

Referring to FIG. 28, a kit 54 for making a veneer in accordance with the present invention includes a composite resin material in a dispenser 56, a bonding agent in a dispenser 58 and an etchant in a dispenser 60. A packaging 62 holds the components of the kit together. Although shown as a pouch, the packaging 62 may be a box or any suitable means for holding the components of the kit together. The kit 54 preferably contains enough material to do one or two teeth. The composite resin material in the dispenser 56 will be of the right shade for the patient's teeth. The dispensers 56-60 are preferably single use containers, such as ampoules. The kit 54 is a single use kit with all of the materials needed to perform an in-office smile makeover in one visit. The kit 54 is preferably shade specific (Shade B1 or Shade A1, etc.). The kit may also include other components such as finishing and polishing discs, a ribbon saw blade for separating the veneer tooth to the adjacent tooth in case of inadvertent splinting and a fast acting whitening gel with dissolvable whitening wraps for preventing inadvertent removal of the whitening gel that is brushed on the facial surfaces of the teeth.

The veneer made by the method of the present invention may be easily repaired in case of chipping. The damaged area and the surrounding area are scuffed up. The tooth is pumiced, etched and rinsed. A thin layer of a bonding agent is applied on the prepared area. A composite resin material of the same shade as the original composite resin material is condensed and placed on the damaged area. A gloved finger is used to move and shape the material. A thin bladed instrument is used to contour the material for enhanced visual illusions. Any excess material is removed to significantly decrease the finishing and polishing after curing. The material is then cured with a curing light. The repaired area is then finished with aluminum oxide discs, aluminum oxide strips, carbide finishing burs and aluminum oxide polishing paste. The result is seamless. Total time expended is about 10-12 minutes.

The method described herein advantageously provide the several benefits to the patient and the dentist.

Ease of placement. Dentists have a limited amount of time in their schedule to perform cosmetic dental services. The method of making a tooth veneer according to the present invention is easy to do and requires only one appointment. In contrast, porcelain veneers require at least two appointments and significant time. Prior art composite veneers are typically too technique sensitive or difficult for the average practitioner and also require significant time to place.

Natural looking results. Patients and dentists want to avoid having smile transformation services that make the patient look like they "had their teeth fixed". The present invention provides veneers that look natural and life like each and every time.

Simplified technical procedures. The present invention has made it easy for anyone to perform the method described herein. Dentists don't want to spend a lot of time placing as well as finishing and polishing veneers. With the present invention, placement is easy and finishing and polishing takes only minutes.

Control of size, shape and illusions. Prior art composite veneers as well as porcelain veneers can appear too large or look like the patient was not born with those teeth. The present invention provides the dentist with a method to control size, shape and illusions that match the patient's adjacent teeth and blend in with their facial features, guaranteeing natural looking results each and every time.

Emergence profile concerns. Unlike conventional composite or porcelain veneers that can cause gingival irritation, a veneer made according to the method of the present invention provides a seamless transition from the root to the clinical crown of the tooth.

Elimination of porosity. Nothing can be more disheartening than placing a conventional composite veneer and to find porosity caused by air bubbles in the material marring the final result. With the veneer made with the method of the present invention, porosity from the air bubbles is eliminated.

An affordable option to porcelain veneers. In today's economic climate, as well as during better economic times, patients are looking for affordable options to transform their smile. The method of the present invention saves patients hundreds of dollars per tooth while providing them with natural looking, white, bright, dazzling smiles.

It is difficult to distinguish between the new veneer system and the patients' natural dentition. At a social distance patients and dentists have a difficult time distinguishing between which teeth are natural and which have veneers.

No need for computer imaging. Computer imaging has its role in dentistry. However computer imaging is not ideally suited for veneers since it can only demonstrate what a computer can achieve under an ideal set of circumstances—not necessarily what the dentist can actually achieve. The method of the present invention as described herein shows the patient exactly what his or her smile will look like—in a manner of just a couple of minutes—and eliminates any guesswork while providing an accurate demonstration of the dentists' artistic talents. It also provides the dentist with a plan of action, with a full understanding of any roadblocks or challenges that might exist in achieving optimum esthetic results. Since computer imaging is not working in real time or dealing with light reflections and other clinical scenarios, computer imaging systems are unable to achieve that.

Simplified maintenance. The veneer made by the present invention may be repaired by any practitioner to maintain a life like and vibrant smile for many years to come—almost indefinitely. With this technology, the new veneer system has an indefinite life span. With porcelain veneers, touch ups typically lead to requiring the removal of the old veneer and the need to replace that veneer with a new veneer. This would require significant time and expense.

A fail proof system that guarantees patient satisfaction each and every time. Conventional porcelain and composite veneers do not guarantee patient satisfaction. When using the method of the present invention, the patient is able to rate her satisfaction with the preview veneer the dentist showed the patient. If the patients' level of expectations are not met based upon the rating given by the patient to the dentist, then the dentist can determine if the patient is a candidate for the veneer procedure. By allowing the patient to rate the preview veneer, the method of the present invention eliminates the disparity between the patient's expectations and the reality of what the dentist can achieve.

Tooth Whitening Method

A tooth whitening method according to the present invention may be used to augment the results of having a tooth veneer made as disclosed herein. As most patients can afford to have a single veneer made to correct one tooth that may not be as attractive as they desire, they may not be able to afford to have 6, 8 or 10 veneers placed. While the non-invasive method of making a tooth veneer according to the present invention provides a methodology to correct the size, shape or appearance of a single tooth using a veneer that may only solve a "tooth" problem but not a "smile" problem that still concerns the patient. This is because the patient does not only want straighter, more even teeth, but they often want whiter, brighter teeth as well. Providing the patient with tooth whitening that brightens the color of the adjacent teeth without tooth sensitivity, uncomfortable isolation or the need to use inconvenient trays that very same day that the veneer is placed provides a valuable tool for the dentist. Along with the method of making a tooth veneer disclosed herein, a tooth whitening method described below becomes a prescription for a same day smile makeover.

Most patients do not like the color of their existing teeth. Traditionally the dentist will provide the patient with either a take home whitening system (includes trays and gel) and have the patient whiten their teeth at home and then return in 2-6 weeks to evaluate the color transformation. Many patients also experience significant sensitivity when whitening their teeth at home. Others find it time consuming and compliance with directions becomes problematic. Once the desired whitening has resulted, the patient must wait an additional two weeks after the whitening is completed in order to achieve maximum bond strength to the tooth when placing the veneer.

An option to this would be for the dentist to do in-office tooth whitening using high concentration peroxide. This would necessitate thorough isolation of the teeth from the oral tissue in order not to produce a chemical burn from the whitening gel on the oral tissue after the high concentration whitening gel is placed on the teeth. In addition to being very expensive, uncomfortable to perform due to the isolation procedures, painful due to "zinger" that many patients experience for up to 24 hours post bleaching, the patient also must wait two weeks after whitening to have the veneers done.

The method for tooth whitening to augment the color of the patient's natural teeth according to the present invention is performed after the in-office veneer using the method described in the present invention is placed. The method for tooth whitening according to the present invention is as follows:

First, the dentist and patient would evaluate the patient's overall smile needs. This includes the use of the non-invasive method of making a tooth veneer of the present invention as disclosed herein as well as the patient's overall desire to have whiter teeth, if any such desire occurs.

Next if the patient would like to whiten their teeth, a shade would be taken of the patients' existing teeth using the Vita Classical Shade Guide (Vident, Brea, Calif.).

It is recommended that the dentist repositions the shade guide tabs according to value order when taking the patient's shade, which would be as follows:

B1, A1, B2, D2, A2, C1, C2, D4, A3, D3, B3, A3.5, B4, C3, A4, C4.

Once the shade is taken and if the patient determines they want whiter teeth, then based upon the starting shade (or the before shade that matches the patient's existing teeth) a shade for the veneer that is anywhere from 1 to 10 shades lighter is selected. The preferred number of shades to whiten the teeth for a same day smile makeover would be from 2 to 4 shades. However it is still feasible to achieve up to 10 shades of whitening with the method of the present invention described below. If a patient chooses to whiten above 4 shades of whitening, they may need to do additional at home whitening after the veneer is placed using a commercially available whitener or one prescribed by the patient's dentist.

After determining if the patient desires to whiten their teeth and a shade for the in-office veneer is consequently determined, the dentist would then proceed to place the in-office veneer using the method described in the present invention. Once the veneer is placed, the dentist would then whiten the patient's teeth to match the color of the patient's new in-office veneer.

First, the dentist would instruct the patient to place a lip balm on their lips. For example, Chap Stick by Pfizer, Madison, N.J. would suffice. There are a variety of commercially available lip balms available that would suffice. The purpose of the lip balm is for added patient comfort during the whitening process.

The dentist would then place a cotton roll between the lip and the gum tissue. One large cotton roll or two smaller cotton rolls for the upper as well as the lower teeth would suffice.

The dentist could also choose to use lip and check retractors to accomplish this isolation.

Figure 29:
FIG. 29 shows the application of whitening gel over the facial surfaces of the patient's teeth.

Next the dentist would apply a tooth whitening gel over the facial surfaces of the teeth, as generally shown in FIG. 29. The gel can be of any desired concentration but would be preferable not to exceed 14%-18% hydrogen peroxide since this process does not require the use of a barrier (such as a rubber dam) or gauze to further isolate the gum and oral tissue.

The gel can be either a carbamide peroxide or hydrogen peroxide material or any other peroxide based material. To eliminate the need to breakdown the peroxide into its constituent elements, the preferred whitening gel is a hydrogen peroxide material delivered in a pen dispenser such as that made by Oratech Manufacturing, South Jordan, Utah. However, the whitening gel can also be dispensed from other vehicles that house the whitening material, such as a compuole or ampoule.

The preferred concentration is about 14% hydrogen peroxide, which has sufficient efficacy for whitening without requiring complete barrier isolation, such as using a rubber dam when applying a 25% hydrogen peroxide gel in the oral cavity. Improper barrier isolation at higher concentrations would lead to a chemical burn and significant irritation to the oral tissues.

Figure 30:
FIG. 30 shows the application of dental whitening wraps or strips to cover the surfaces of the patient's teeth after the application of the whitening gel.

After the whitening gel is applied to the teeth that are isolated from the lips with a simple lip balm and cotton roll combination, the dentist will then immediately place dental whitening wraps or whitening strips to cover the surfaces of the teeth, as generally shown in FIG. 30. The dental whitening wraps function as the thinnest tray commercially available to cover the surfaces of the teeth. The whitening wraps or strips will further isolate the peroxide gel from the oral tissues, providing a barrier that advantageously prevents the hydrogen peroxide gel from contacting the oral tissues, such as the lips, tongue and saliva and prevents frictional removal of the initial whitening gel before it has had sufficient time to break down into its constituent elements and remove the offending stains.

The dental whitening wraps or whitening strips contain whitening preparations and are commercially available products, such as a non-dissolvable whitening strip from Crest WhiteStrips, P&G, Cincinnati, Ohio or a dissolvable whitening wraps from Ranir LLC, Grand Rapids, Mich. The preferred whitening wraps or strips for isolation purposes for the present invention are the dissolvable whitening wraps from Ranir LLC. The reason is because of synchronicity. As described below, a significant portion of whitening is accomplished in 5 to 10 minutes. The dissolvable whitening wraps also dissolve in 5 to 10 minutes. This synchronizes the entire system and essentially creates a built-in intelligence relative to knowing when the whitening is completed.

For additional whitening benefits the patient can leave the gel on their teeth for an another 5 to 10 minutes.

Furthermore the use of a whitening wraps or strips that contain no peroxide would also be sufficient for isolation purposes. However, the use of a whitening wraps or strips containing peroxide is to augment the results of the whitening process. The patient would be receiving tooth whitening from both the hydrogen peroxide gel as well as from the whitening preparations contained in the whitening wraps or strips.

The patient would allow the peroxide combination to remain on their teeth for a period from 1 minute to 30 minutes, allowing the whitening gel to breakdown and release oxygen free radicals that remove the discoloring stains both superficially as well as deeper into the tooth structure. The preferred time for use in the present invention is from 5 to 10 minutes.

During the 5 to 10 minute interval as the tooth whitening is occurring, the patient can remove the cotton rolls for additional comfort if so desired.

After the first 5 to 10 minute application is completed, the dentist will then assess if the color of the whitened teeth match the color of the newly placed in-office veneer. If the veneer is still lighter in shade, the dentist would then remove any residual whitening gel from the teeth and using the same simplified isolation system described above (with lip balm and cotton rolls) the dentist would apply additional whitening gel in the manner described above, and further isolating the teeth with the whitening wraps or strips.

This process can be repeated up to 4-5 times during the patient's single visit. Once the dentist and patient determine that the shade of the veneer matches the whitened teeth, there would be no need to do additional whitening applications.

The use of the method of first placing the veneer on the teeth and then whitening the teeth can provide patients with the same day smile transformation that they desire. The benefits of instant results at an affordable price without the discomfort (both procedural and post-operative) associated with conventional in-office tooth whitening and eliminating the long wait time associated with at-home whitening and then placing the veneer will significantly enhance the desired outcome for patients—whiter, straighter, even teeth done in one easy visit.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

I claim:

1. A non-invasive method for making a tooth veneer from composite resin material for a patient's tooth without tooth reduction, enamel removal or any invasive tooth preparation, comprising the steps of:
    a) transferring an amount of composite resin material on the patient's tooth without prior invasive tooth preparation;
    b) forming a preview veneer from the composite resin material directly on the tooth at a position, including extending the preview veneer onto an incisal surface of the tooth to provide a positioning stop as a guide when the preview veneer is removed and re-positioned at the same position and bonded to the tooth;
    c) requesting the patient to approve or disapprove the preview veneer;
    d) removing the preview veneer;
    e) bonding the preview veneer to the tooth at the same position, including using the positioning stop to re-position the preview veneer at the same position; and
    f) removing the positioning stop.

2. A non-invasive method as in claim 1, and further comprising the step of heat treating the preview veneer after removal in a microwave oven in a bath of water prior to the step of bonding.

3. A non-invasive method as in claim 1, and further comprising the step of removing air bubbles from the composite resin material prior to the step of transferring.

4. A non-invasive method as in claim 3, wherein the step of removing air bubbles includes the step of compressing the composite resin material several times between gloved fingers of the dentist.

5. A non-invasive method as in claim 1, wherein the step of forming includes the step of removing any excess composite resin material from a lingual surface of the tooth.

6. A non-invasive method as in claim 1, wherein the step of forming includes the step of placing the composite resin material on the middle of a facial surface of the tooth.

7. A non-invasive method as in claim 6, wherein the step of forming includes the step of moving the composite resin material toward an incisal edge of the tooth to make the tooth appear longer.

8. A non-invasive method as in claim 6, wherein the step of forming includes the step of moving the composite resin material away from an incisal edge of the tooth to make the tooth appear shorter.

9. A non-invasive method as in claim 6, wherein the step of forming includes the step of moving the composite resin material toward an interproximal surface of the tooth to make the tooth appear wider.

10. A non-invasive method as in claim 6, wherein the step of forming includes the step of moving the composite resin material away from an interproximal surface of the tooth to make the tooth appear narrower.

11. A non-invasive method as in claim 6, wherein the step of forming includes the step of moving the composite resin material toward a gingival half of the tooth.

12. A non-invasive method as in claim 6, wherein the step of forming includes the step of shaping the composite resin material over the tooth.

13. A non-invasive method as in claim 12, wherein the step of forming includes the step of curing the composite resin material with a curing light.

14. A non-invasive method as in claim 13, wherein the step of curing includes the step of curing in segments; namely, gingival, incisal, middle of the facial, distal and mesial segments of the tooth.

15. A non-invasive method as in claim 14, wherein the step of curing includes the step of curing each segment about 10-20 seconds.

16. A non-invasive method as in claim 12, wherein the step of shaping includes the step of making the preview veneer translucently thin.

17. A non-invasive method as in claim 6, wherein the step of forming includes the step of removing any excess composite resin material from the tooth.

18. A non-invasive method as in claim 6, wherein the step of forming includes the step of adding more composite resin material to the tooth as needed.

19. A non-invasive method as in claim 1, wherein the step of bonding includes the step of:
   a) applying etchant on the tooth;
   b) applying a bonding agent on the tooth;
   c) roughing an inside surface of the preview veneer;
   d) applying etchant on the inside surface of the preview veneer;
   e) applying a bonding agent on the inside surface of the preview veneer;
   f) applying a luting material on the inside surface of the preview veneer; and
   g) attaching the preview veneer to the tooth.

20. A non-invasive method as in claim 1, wherein the step of requesting includes the step of asking the patient to rate the preview veneer by a score of A, B, C, D or F, wherein a score of A or B means approval by the patient.

21. A non-invasive method as in claim 1, and further comprising the step of consulting with the patient prior to coming to see the dentist.

22. A non-invasive method as in claim 21, where the step of consulting includes the step of asking the patient to send photographs to the dentist showing the patient's full face, close-up of the patient's teeth wide open on the left and right sides, frontal close-up of the patient's teeth slightly apart, and a close-up of the patient's front upper and lower teeth biting edges touching edge-to-edge.

23. A method as in claim 1, and further comprising the step of providing tooth whitening to the patient's teeth after bonding the preview veneer to the tooth in step e) to match the preview veneer.

24. A method as in claim 23, wherein the step of providing tooth whitening comprises the steps of:
   a) applying whitening gel over at least front surfaces of the teeth; and
   b) applying a whitening wrap or strip to cover the at least front surfaces of the teeth.

25. A method as in claim 24, wherein:
   a) the step of applying the whitening gel includes a whitening gel having about 14-18% hydrogen peroxide; and
   b) the step of applying whitening wrap or strip includes a dissolvable whitening wrap or strip.

* * * * *